(12) United States Patent
Hirose

(10) Patent No.: US 9,115,972 B2
(45) Date of Patent: Aug. 25, 2015

(54) OPTICAL TOMOGRAPHIC IMAGING APPARATUS AND IMAGING METHOD THEREFOR TO ACQUIRE IMAGES INDICATING POLARIZATION INFORMATION

(75) Inventor: Futoshi Hirose, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 120 days.

(21) Appl. No.: 13/808,895

(22) PCT Filed: Jul. 4, 2011

(86) PCT No.: PCT/JP2011/003798
§ 371 (c)(1),
(2), (4) Date: Jan. 7, 2013

(87) PCT Pub. No.: WO2012/004967
PCT Pub. Date: Jan. 12, 2012

(65) Prior Publication Data
US 2013/0107272 A1   May 2, 2013

(30) Foreign Application Priority Data

Jul. 9, 2010   (JP) ................................ 2010-156919

(51) Int. Cl.
*G01B 9/02* (2006.01)
*A61B 3/10* (2006.01)
*A61B 5/00* (2006.01)

(52) U.S. Cl.
CPC ............ *G01B 9/02011* (2013.01); *A61B 3/102* (2013.01); *A61B 5/0066* (2013.01);
(Continued)

(58) Field of Classification Search
CPC .. A61B 3/102; A61B 5/0066; G01B 9/02091; G01B 2290/70; G01B 9/02011; G01B 9/02044; G01B 9/02027; G01B 2290/65

USPC ................. 356/479, 477, 512, 491–497, 327
See application file for complete search history.

(56) References Cited

U.S. PATENT DOCUMENTS

| | | | |
|---|---|---|---|
| 5,719,399 A | 2/1998 | Alfano et al. | |
| 6,399,938 B1 | 6/2002 | Sugawara et al. | |

(Continued)

FOREIGN PATENT DOCUMENTS

| | | |
|---|---|---|
| CN | 1917806 A1 | 2/2007 |
| CN | 101433458 A | 5/2009 |

(Continued)

OTHER PUBLICATIONS

Bernhard Baumann, Erich Götzinger, Michael Pircher, and Christoph K. Hitzenberger, Single camera based spectral domain polarization sensitive optical coherence tomography, Optics Express, Feb. 5, 2007, vol. 15, No. 3, p. 1054-1063.*

(Continued)

*Primary Examiner* — Michael A Lyons
*Assistant Examiner* — Violeta A Prieto
(74) *Attorney, Agent, or Firm* — Canon USA Inc IP Division

(57) ABSTRACT

An imaging apparatus adjusts the polarization directions of irradiation beams (to a diffraction grating) corresponding to first and second beams respectively which have different polarization directions (for example, by adjusting a relative angle formed between light-emitting ends of respective polarization maintaining fibers) so that the spectral characteristics of the irradiation beams at the diffraction grating coincide with each other. Then, the imaging apparatus acquires a tomographic image indicating polarization information for a object based on beams (that come from the diffraction grating for splitting and diffracting a beam from the adjustment unit) corresponding to the first and second beams respectively which have different polarization directions.

9 Claims, 5 Drawing Sheets

(52) U.S. Cl.
CPC ........ *G01B9/02027* (2013.01); *G01B 9/02044* (2013.01); *G01B 9/02091* (2013.01); *G01B 2290/65* (2013.01); *G01B 2290/70* (2013.01)

(56) References Cited

U.S. PATENT DOCUMENTS

| | | | |
|---|---|---|---|
| 7,576,866 B2 * | 8/2009 | Ohkubo | 356/479 |
| 7,625,088 B2 | 12/2009 | Fujita et al. | |
| 7,648,242 B2 | 1/2010 | Ferguson et al. | |
| 7,973,939 B2 | 7/2011 | Chou | |
| 8,334,982 B2 | 12/2012 | Fang-Yen et al. | |
| 8,376,547 B2 | 2/2013 | Hirose | |
| 8,427,654 B2 | 4/2013 | Horn et al. | |
| 8,463,016 B2 | 6/2013 | Pang | |
| 8,602,556 B2 | 12/2013 | Imamura | |
| 8,622,547 B2 | 1/2014 | Hayashi | |
| 8,764,737 B2 | 7/2014 | Kurtz et al. | |
| 2002/0091323 A1 | 7/2002 | Dreher | |
| 2007/0038040 A1 | 2/2007 | Cense et al. | |
| 2007/0070295 A1 | 3/2007 | Tsukada et al. | |
| 2007/0109554 A1 | 5/2007 | Feldchtein et al. | |
| 2007/0115481 A1 | 5/2007 | Toth et al. | |
| 2007/0211255 A1 * | 9/2007 | Ohkubo | 356/479 |
| 2007/0237445 A1 | 10/2007 | Hatori | |
| 2008/0100612 A1 | 5/2008 | Dastmalchi et al. | |
| 2008/0151187 A1 | 6/2008 | Tsukada et al. | |
| 2008/0285043 A1 | 11/2008 | Fercher | |
| 2009/0115964 A1 | 5/2009 | Ueno | |
| 2009/0247862 A1 | 10/2009 | Meyer et al. | |
| 2009/0310083 A1 | 12/2009 | Campbell et al. | |
| 2010/0166293 A1 | 7/2010 | Sugita et al. | |
| 2011/0137157 A1 | 6/2011 | Imamura et al. | |
| 2011/0228222 A1 | 9/2011 | Kobayashi | |
| 2011/0267340 A1 | 11/2011 | Kraus et al. | |
| 2011/0299034 A1 | 12/2011 | Walsh et al. | |
| 2012/0026464 A1 | 2/2012 | Berger et al. | |
| 2012/0140170 A1 | 6/2012 | Hirose et al. | |
| 2012/0249956 A1 | 10/2012 | Narasimha-Iyer et al. | |
| 2013/0003077 A1 | 1/2013 | Suehira et al. | |
| 2013/0070202 A1 | 3/2013 | Yonezawa et al. | |
| 2013/0107277 A1 * | 5/2013 | Hirose et al. | 356/512 |
| 2013/0182259 A1 | 7/2013 | Brezinski et al. | |
| 2013/0258349 A1 | 10/2013 | Makihira et al. | |
| 2013/0301006 A1 | 11/2013 | Kim et al. | |

FOREIGN PATENT DOCUMENTS

| | | |
|---|---|---|
| CN | 101986185 A | 3/2011 |
| CN | 102264281 A | 11/2011 |
| JP | 2007-240228 A | 9/2007 |
| JP | 2008-508068 A | 3/2008 |
| JP | 2008-241585 A | 10/2008 |
| JP | 2008-264048 A | 11/2008 |
| JP | 2008-272256 A | 11/2008 |
| JP | 2010-012111 A | 1/2010 |
| JP | 2010-029648 A | 2/2010 |
| JP | 2010-125291 A | 6/2010 |
| JP | 2011-212232 A | 10/2011 |
| RU | 2344764 C1 | 1/2009 |
| WO | 2007/103115 A2 | 9/2007 |
| WO | 2008129864 A1 | 10/2008 |
| WO | 2008/139799 A1 | 11/2008 |
| WO | 2010/074279 A1 | 7/2010 |
| WO | 2010/101162 A1 | 9/2010 |
| WO | 2010122118 A1 | 10/2010 |
| WO | 2012/004970 A1 | 1/2012 |

OTHER PUBLICATIONS

D. A. Zimnyakov, V. V. Tuchin, Optical Tomography of Tissues, Quantum Electronics, 2002, 32(10):849-865, Kvantovaya Elektronika and Turpion Ltd, Moscow, RU, 2002.

Erich Götzinger et al., High Speed Spectral Domain Polarization Sensitive Optical Coherence Tomography of the Human Retina, Optics Express, Dec. 12, 2005, 13(25):10217-10229, Optical Society of America, Washington, D.C, 2005.

U.S. Appl. No. 13/808,888, filed Jan. 7, 2013, Futoshi Hirose.
U.S. Appl. No. 13/742,666, filed Jan. 16, 2013, Yoshihiko Iwase.
U.S. Appl. No. 13/742,738, filed Jan. 16, 2013, Yoshihiko Iwase.
U.S. Appl. No. 13/742,834, filed Jan. 16, 2013, Yoshihiko Iwase.
U.S. Appl. No. 13/743,083, filed Jan. 16, 2013, Yoshihiko Iwase.
U.S. Appl. No. 13/743,153, filed Jan. 16, 2013, Yoshihiko Iwase.
U.S. Appl. No. 13/743,216, filed Jan. 16, 2013, Yoshihiko Iwase.

Erich Götzinger et al., Polarization Maintaining Fiber Based Ultra-High Resolution Spectral Domain Polarization Sensitive Optical Coherence Tomography, Optics Express vol. 17, No. 25; pp. 22704-22717, Optical Society of America, Washington, D.C., Nov. 25, 2009.

Mircea Mujat et al., Autocalibration of spectral-domain optical coherence tomography spectrometers for in vivo quantitative retinal nerve fiber layer birefringence determination, Journal of Biomedical Optics, vol. 12, issue 4, article 041205, Jul. 30, 2007, Society of Photo-Optical Instrumentation Engineers, Bellingham WA, 2007.

Erich Götzinger, Michael Pircher, Wolfgang Geitzenauer, Christian Ahlers, Bernhard Baumann, Stephan Michels, Ursula Schmidt-Erfurth, Christoph K. Hitzenberger, Retinal Pigment Epithelium Segmentation by Polarization Sensitive Optical Coherence Tomography, Optics Express, Oct. 15, 2008, 16(21):16410-16422, Optical Society of America, Washington DC, 2008.

E. Götzinger, M. Pircher, B. Baumann, C. Hirn, C. Vass, C, K. Hitzenberger, Retinal Nerve Fiber Layer Birefringence Evaluated With Polarization Sensitive Spectral Domain OCT and Scanning Laser Polarimetry: A Comparison, Journal of Biophotonics, Feb. 18, 2008, 1(2):129-139, WILEY-VCH Verlag GmbH & Co. KGaA, Weinheim, DE, 2008.

* cited by examiner

OPTICAL TOMOGRAPHIC IMAGING APPARATUS AND IMAGING METHOD THEREFOR TO ACQUIRE IMAGES INDICATING POLARIZATION INFORMATION

TECHNICAL FIELD

The present invention relates to an optical tomographic imaging apparatus and an imaging method for the optical tomographic imaging apparatus. More particularly, the present invention relates to an optical tomographic imaging apparatus for capturing tomographic images used for ophthalmologic examinations, and to an imaging method for the optical tomographic imaging apparatus.

BACKGROUND ART

Optical coherence tomography (OCT) using the multiple-wavelength optical interference is a method for obtaining a high-resolution tomographic image of a sample (particularly, the fundus). Hereinafter, an apparatus for capturing a tomographic image by using OCT is referred to as OCT apparatus.

In recent years, OCT apparatuses for ophthalmology have attempted to acquire a functional OCT image for imaging the optical characteristics and movement of the fundus tissue in addition to an ordinary OCT image for imaging the shape of the fundus tissue. A polarization OCT apparatus, one type of the above-mentioned functional OCT apparatus, performs imaging by using polarization parameters (retardation and orientation) which are optical characteristics of the fundus tissue. By using polarization parameters, the polarization OCT apparatus can form a polarization OCT image and make a distinction or perform segmentation of the fundus tissue. The polarization OCT apparatus uses a circularly-polarized beam or polarization-modulated beam as a measuring beam for observing a sample, and splits an interference beam into two orthogonal linearly-polarized beams.

A technique for acquiring a high-resolution polarization OCT image by using a polarization OCT apparatus having two spectroscopes and a wide-wavelength light source is discussed in Non Patent Literature 1. This technique renders a tomographic image in which the retinal pigment epithelium layer is distinguished from the fundus tissue by using acquired polarization parameters. It is known that depolarization (randomization of polarization) takes place in the retinal pigment epithelium layer. The polarization OCT apparatus uses two different diffraction gratings for two interference beams having different polarization directions (orthogonal linearly-polarized beams).

A polarization OCT apparatus for detecting two interference beams by inputting two interference beams having different polarization directions to one spectroscope is discussed in Non Patent Literature 2. Thus, the polarization OCT apparatus can be downsized and control procedure can be simplified.

Generally, the diffraction efficiency of a diffraction grating, one type of spectroscopes, depends on the polarization direction. Therefore, beams having different polarization directions differ in spectral characteristics at a diffraction grating (incidence beam polarization directions with respect to the diffraction grating), resulting in different sensitivities of the diffraction grating. Thus, the accuracy in polarization parameter calculation is affected.

CITATION LIST

Non Patent Literature

NPL 1: "Polarization maintaining fiber based ultra-high resolution spectral domain polarization sensitive optical coherence tomography" Opt. Express 17, 22704 (2009)

NPL 2: "Autocalibration of spectral-domain optical coherence tomography spectrometers for in vivo quantitative retinal nerve fiber layer birefringence determination" J. Biomed. Opt., 12, 041205 (2007)

SUMMARY OF INVENTION

The present invention is directed to providing an optical tomographic imaging apparatus capable of acquiring accurate polarization parameters with a simplified optical setup to acquire a polarization OCT image, and an imaging method for the optical tomographic imaging apparatus.

According to an aspect of the present invention, the optical tomographic imaging apparatus according to the present invention includes a splitting unit configured to split a combined beam into first and second beams having different polarization directions, the combined beam being formed by combining a return beam from a object with a reference beam corresponding to the measuring beam, the object being irradiated with the measuring beam. The optical tomographic imaging apparatus further includes an adjustment unit configured to adjust the polarization directions of irradiation beams (to a diffraction grating) corresponding to the first and second beams respectively so that the spectral characteristics of the irradiation beams at the diffraction grating coincide with each other and an acquisition unit configured to acquire a tomographic image indicating polarization information for the object based on the beams (from the diffraction grating for splitting and diffracting a beam from the adjustment unit) corresponding to the first and the second beams respectively.

According to the present invention, the spectral characteristics (incidence beam polarization directions with respect to the diffraction grating) of beams having different polarization directions can be aligned. Thus, an optical tomographic imaging apparatus capable of acquiring accurate polarization parameters with a simplified optical setup to acquire a polarization OCT image, and an imaging method for the optical tomographic imaging apparatus can be achieved.

Further features and aspects of the present invention will become apparent from the following detailed description of exemplary embodiments with reference to the attached drawings.

BRIEF DESCRIPTION OF DRAWINGS

The accompanying drawings, which are incorporated in and constitute a part of the specification, illustrate exemplary embodiments, features, and aspects of the invention and, together with the description, serve to explain the principles of the invention.

DESCRIPTION OF EMBODIMENTS

Various exemplary embodiments, features, and aspects of the invention will be described in detail below with reference to the drawings.

Figure 1:
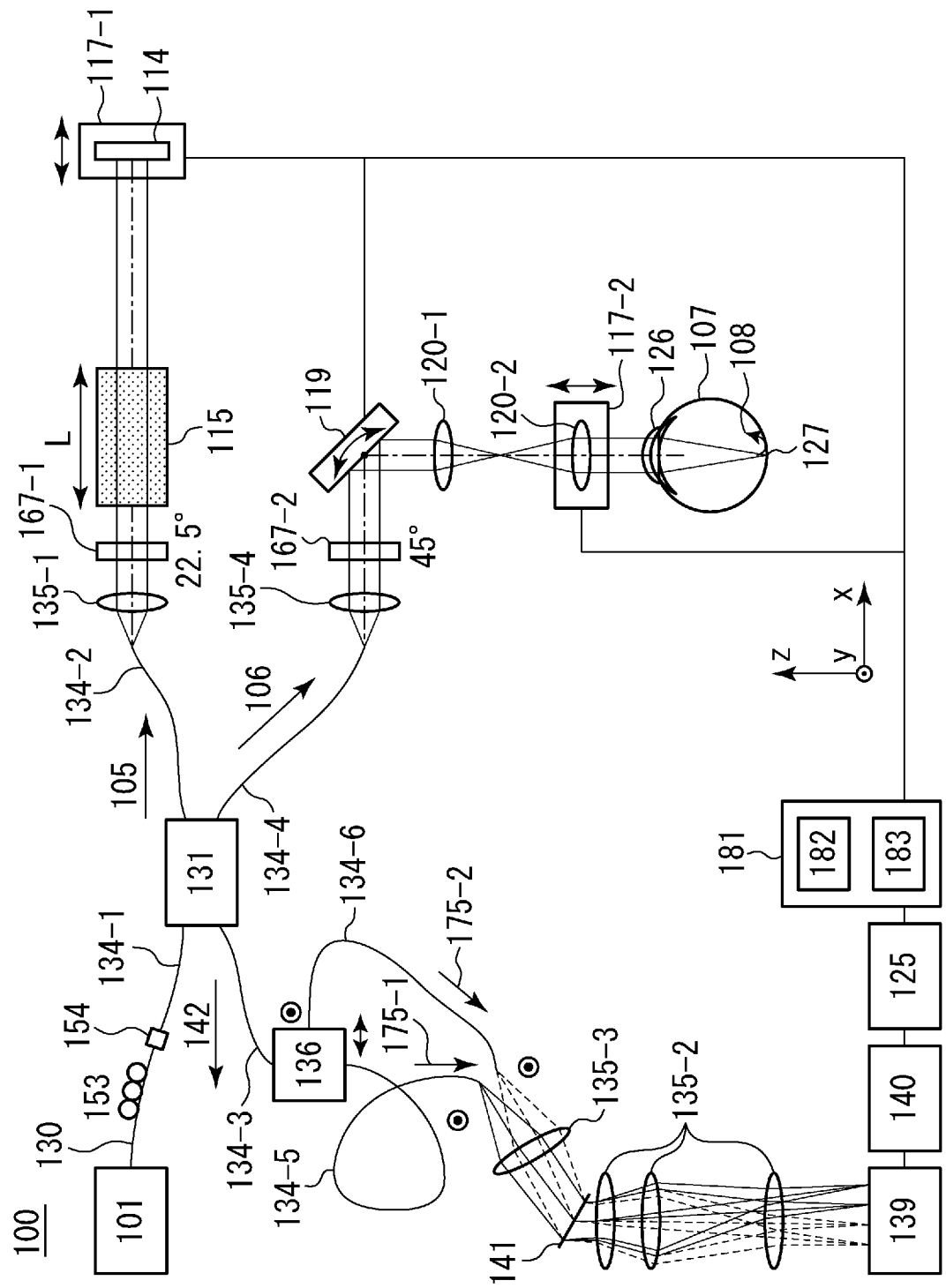
FIG. 1 illustrates a configuration of an OCT apparatus according to a first exemplary embodiment of the present invention.

An imaging apparatus according to the present exemplary embodiment will be described below with reference to FIG. 1. FIG. 1 illustrates a configuration of an OCT apparatus 100 (particularly, a polarization OCT apparatus) according to the present exemplary embodiment.

A return beam 108 comes from a object 107 irradiated with a beam based on a measuring beam 106 (a circularly-polarized beam obtained after the measuring beam 106 passes through a lambda/4 plate 167-2 disposed with a 45-degree inclination with respect to a measuring beam path). The return beam 108 is combined with a beam based on a reference beam 105 corresponding to the measuring beam 106 (a linearly-polarized beam obtained after the reference beam 105 passes through a lambda/4 plate 167-1 disposed with a 22.5-degree inclination with respect to a reference beam path) to form a combined beam 142. The combined beam 142 is split into a first beam 175-1 and a second beam 175-2 having different polarization directions, by a splitting unit 136.

Then, the OCT apparatus 100 adjusts the polarization directions of irradiation beams to a diffraction grating (for example, a light transmission type grating 141) respectively corresponding to the first beam 175-1 and the second beam 175-2 having different polarization directions. For example, the OCT apparatus 100 adjusts a relative angle formed between a light-emitting end of a first polarization maintaining fiber 134-5 and a light-emitting end of a second polarization maintaining fiber 134-6. In this case, adjustment is made so that the spectral characteristics of the irradiation beams at the diffraction grating 141 (incidence beam polarization directions with respect to the diffraction grating 141) coincide with each other. When performing the above-mentioned adjustment, it is desirable to irradiate the diffraction grating 141 with the first beam 175-1 and the second beam 175-2 with polarization directions aligned.

Then, the OCT apparatus 100 acquires a tomographic image (also referred to as polarization OCT image) indicating polarization information of the object 107 based on the beams (from the diffraction grating 141 for splitting and diffracting a beam from the above-mentioned adjustment unit) respectively corresponding to the first beam 175-1 and the second beam 175-2 having different polarization directions.

Thus, the polarization directions of incidence beams with respect to the diffraction grating 141 can be aligned with each other. Therefore, since the reduction in diffraction efficiency of the diffraction grating 141 due to the polarization dependency can be prevented, accurate polarization parameters can be acquired to obtain a polarization OCT image with a simplified optical setup.

It is desirable to provide a detection unit (for example, a line sensor 139) for detecting, in different detection areas, beams (from the spectral unit 141) respectively corresponding to the first beam 175-1 and the second beam 175-2. Thus, the plurality of beams can be detected by the common detection unit 139. Thus, a tomographic image indicating intensity information of the object 107 can be acquired based on outputs (from the detection areas of the detection unit 139) respectively corresponding to the first beam 175-1 and the second beam 175-2.

Further, it is desirable to irradiate an irradiation position at the diffraction grating 141 for the beam from the adjustment unit (for example, the light-emitting end of the first polarization maintaining fiber 134-5) corresponding to the first beam 175-1 with the beam from the adjustment unit corresponding to the second beam 175-2. Thus, the OCT apparatus 100 can be configured with one diffraction grating and therefore can be of smaller size than an apparatus using two diffraction gratings.

A configuration implementing the present invention will be described below based on the following exemplary embodiments.

In the first exemplary embodiment, the OCT apparatus 100 to which the present invention is applied will be described below. In the present exemplary embodiment, the object 107 is irradiated with a circularly-polarized measuring beam from a light source 101, and the return beam 108 based on the measuring beam 106 radiated onto the object 107 is combined with the reference beam 105 to produce an interference beam. Then, the interference beam is split into two linearly-polarized beams and measured, thus forming an optical tomographic imaging apparatus capable of capturing a polarization tomographic image of the object 107, i.e., a polarization OCT apparatus.

The OCT apparatus 100 inputs interference beams with aligned polarization directions with respect to the diffraction grating 141 to optimize its diffraction efficiency, enabling the acquisition of more accurate polarization parameters.

An overall configuration of the OCT apparatus 100 according to the present exemplary embodiment will be described below with reference to FIG. 1. As illustrated in FIG. 1, the OCT apparatus 100 according to the present exemplary embodiment totally configures the Michelson interferometer and includes a number of optical paths formed of polarization maintaining fibers capable of maintaining beam polarization direction.

Referring to FIG. 1, a beam emitted from the light source 101 passes through a polarization maintaining fiber 134-1, reaches an optical coupler 131, and then is split into the reference beam 105 and the measuring beam 106 in an intensity ratio of 90:10 by the optical coupler 131. The measuring beam 106 passes through a polarization maintaining fiber 134-4, a XY scanner 119, and lenses 120-1 and 120-2, and then is led to the subject's eye 107 (sample under observation).

The measuring beam 106 is reflected or scattered by the subject's eye 107 (sample under observation) to become the return beam 108. Then, the return beam 108 is combined with the reference beam 105 having passed through the reference beam path by the optical coupler 131.

After the return beam 108 is combined with the reference beam 105, the resultant combined beam 142 is split and diffracted for respective wavelengths by the light transmission type grating 141 and then input to the line camera 139. The line camera 139 converts optical intensity into a voltage for respective positions (wavelengths), and a personal computer 125 uses resultant signals to form a tomographic image of the subject's eye 107. Motor-driven stages 117-1 and 117-2 and the XY scanner 119 are controlled by the personal computer 125 via a driver unit 181.

Circumferences of the light source 101 will be described below. The light source 101 is a super luminescent diode (SLD) which is a typical low-coherent light source having a wavelength of 830 nm and a bandwidth of 50 nm. The bandwidth is an important parameter since it affects the resolution in the optical axis direction of the obtained tomographic image. Although an SLD is selected as the light source 101 according to the present exemplary embodiment, the light source 101 is not limited thereto, but may be any type of light source as long as it emits a low-coherent beam, for example, an amplified spontaneous emission (ASE) light source. Further, in consideration of eye measurement, the wavelength of the near-infrared ray is suitable. Further, since the wavelength affects the resolution in the horizontal direction of the obtained tomographic image, it is desirable to use an as short wavelength as possible. In the present exemplary embodiment, a wavelength of 830 nm is used. However, other wavelengths may be selected depending on the measuring portion under observation.

The beam emitted from the beam source 101 passes through a single mode fiber 130, a polarization controller 153, a connector 154, and a polarization maintaining fiber 134-1, and then is led to the optical coupler 131. The polarization controller 153 plays a role of adjusting the polarization state of the emitted beam. In the present exemplary embodiment, the polarization state is adjusted to linearly-polarized beams in the Y-axis direction (direction perpendicular to paper).

Optical paths of the reference beam 105 will be described below.

The reference beam 105 formed by the optical coupler 131 passes through a polarization maintaining fiber 134-2 and then is led to a lens 135-1. Then, the reference beam 105 is adjusted to become a parallel beam having a 1-mm beam diameter by the lens 135-1. The reference beam 105 is a linearly-polarized beam in the Y-axis direction.

Then, the reference beam 105 passes through a lambda/4 plate 167-1 (also referred to as first change unit) and a dispersion compensation glass 115 and then is led to a reference mirror 114. Since the optical pathlength for the reference beam 105 is adjusted to become approximately the same as the optical pathlength for the measuring beam 106, the reference beam 105 can be caused to interfere with the measuring beam 106. Then, the reference beam 105 is reflected by the reference mirror 114 and then led again to the optical coupler 131.

The lambda/4 plate 167-1 is disposed so that its fast axis is inclined by 22.5 degrees with respect to the Y-axis direction. The reference beam 105 passes through the lambda/4 plate 167-1 twice to become a linearly-polarized beam inclined by 45 degrees with respect to the Y-axis direction. The linearly-polarized beam inclined by 45 degrees contains a linearly-polarized beam in the X-axis direction and a linearly-polarized beam in the Y-axis direction.

The reference beam 105 passes through the dispersion compensation glass 115 which compensates the dispersion occurring when the measuring beam 106 travels back and forth between the subject's eye 107 and the lenses 120-1 and 120-2. The diameter of the eyeball, L, is set to 24 mm which is an average value of Japanese.

The motor-driven stage 117-1 is movable in directions denoted by arrows, making possible the adjustment of the optical pathlength for the reference beam 105. The motor-driven stage 117-1 can be controlled by the personal computer 125 via a motor-driven stage driver 183 in the driver unit 181.

Optical paths of the measuring beam 106 will be described below.

The measuring beam 106 formed by the optical coupler 131 passes through the polarization maintaining fiber 134-4 and then is led to the lens 135-4. Then, the measuring beam 106 is adjusted to become a parallel beam having a 1-mm beam diameter by the lens 135-4. The measuring beam 106 passes through the lambda/4 plate 167-2 (also referred to as second change unit), reflect off the XY scanner 119, passes through the lenses 120-1 and 120-2, and enters the subject's eye 107.

The lambda/4 plate 167-2 is disposed so that its fast axis is inclined by 45 degrees with respect to the Y-axis direction. The measuring beam 106 passes through the lambda/4 plate 167-2 to become a circularly-polarized beam before entering the subject's eye 107. The circularly-polarized beam contains a linearly-polarized beam in the X-axis direction and a linearly-polarized beam in the Y-axis direction, having a 90-degree phase difference therebetween.

Although the XY scanner 119 is described as one mirror to simplify description, it is actually formed of two mirrors (an X-scanning mirror and a Y-scanning mirror) disposed close to each other to raster-scan a retina 127 in a direction perpendicular to the optical axis. A center of the measuring beam 106 is adjusted to coincide with the rotational center of the mirror of the XY scanner 119. The XY scanner 119 is controlled by the personal computer 125 via an optical scanner driver 182 in the driver unit 181.

The lenses 120-1 and 120-2 form an optical system having a role of scanning the retina 127 by deflecting the measuring beam 106 using a vicinity of a cornea 126 as a fulcrum. Each of the lenses 120-1 and 120-2 has a focal length of 50 mm. Although the lens 120-2 is a spherical lens, it may be a cylindrical lens and a new lens may be added to the optical path of the measuring beam 106 depending on the optical aberration (refractive error) of the subject's eye 107. The use of a cylindrical lens is effective when the subject's eye 107 has astigmatism.

The motor-driven stage 117-2 is movable in directions denoted by arrows to adjust and control the position of the lens 120-2 accompanying the motor-driven stage 117-2. The motor-driven stage 117-2 is controlled by the personal computer 125 via the motor-driven stage driver 183 in the driver unit 181. By adjusting the position of the lens 120-2, the measuring beam 106 can be condensed to a predetermined layer of the retina 127 of the subject's eye 107 to enable the observation of the retina 127. Adjusting the position of the lens 120-2 also enables coping with a case where the subject's eye 107 has a refractive error.

When the measuring beam 106 enters the subject's eye 107, the return beam 108 is produced by reflection and scattering from the retina 127. The reference beam 105 is combined with the return beam 108 by the optical coupler 131 and then the resultant combined beam 142 is further split in an intensity ratio of 90:10.

A configuration of a measurement system in the OCT apparatus 100 according to the present exemplary embodiment will be described below. The combined beam 142 formed by the optical coupler 131 passes through a polarization maintaining fiber 134-3 and then is led to a polarization coupler 136. The combined beam 142 is split into two split beams 175-1 and 175-2 (orthogonal linearly-polarized beams) by the polarization coupler 136.

The split beam 175-1 (a linearly-polarized beam in the X-axis direction (direction in parallel with paper plane)) passes through the first polarization maintaining fiber 134-5 and then is input to a lens 135-3. A light-emitting end of the first polarization maintaining fiber 134-5 is disposed so that the split beam 175-1 is emitted therefrom as a linearly-polarized beam in the Y-axis direction (direction perpendicular to paper plane) with respect to the lens 135-3.

The split beam 175-2 (a linearly-polarized beam in the Y-axis direction) passes through the second polarization maintaining fiber 134-6 and then is input to the lens 135-3. The light-emitting end of the second polarization maintaining fiber 134-6 is disposed so that the split beam 175-2 is emitted therefrom to the lens 135-3 as a linearly-polarized beam in the Y-axis direction.

Specifically, the light-emitting ends of the first polarization maintaining fiber 134-5 and the second polarization maintaining fiber 134-6 are held so that the split beams 175-1 and 175-2 are emitted therefrom, respectively, in the above mentioned polarization directions.

The split beams 175-1 and 175-2 reach the same position on the light transmission type grating 141 at different incident angles, and are split and diffracted for respective wavelengths by the light transmission type grating 141. The resultant split beams are condensed by lenses 135-2 and then reach different positions of the line camera 139. Each of the split beams 175-1 and 175-2 enters the light transmission type grating 141 in the same polarization direction (as a linearly-polarized beam in the Y-axis direction). Therefore, it becomes unnecessary to take into consideration the polarization dependence of the diffraction efficiency of the light transmission type grating 141, enabling the optimization to a polarized beam (a linearly-polarized beam in the Y-axis direction) input to the light transmission type grating 141.

The line camera 139 detects the light intensity of each of the split beams 175-1 and 175-2 for respective positions (wavelengths). Specifically, a spectrum area interference fringe on the wavelength axis can be observed by the line camera 139.

The detected light intensity is input to the personal computer 125 via a frame grabber 140. The personal computer 125 performs data processing to form a tomographic image and displays it on a display screen (not illustrated).

The line camera 139 is provided with 2048 pixels to obtain the light intensity for respective wavelengths (1024 divisions) of each of the split beams 175-1 and 175-2.

In the present exemplary embodiment, although each of the split beams 175-1 and 175-2 enters the light transmission type grating 141 as a linearly-polarized beam in the Y-axis direction, the optical setup is not limited thereto as long as polarization directions of the split beams 175-1 and 175-2 coincide with each other, whatever the polarization direction.

A method for acquiring a tomographic image by using the OCT apparatus 100 will be described below with reference to FIGS. 2A to 2C.

The OCT apparatus 100 controls the XY scanner 119 to acquire an interference fringe by using the line camera 139, thus acquiring a tomographic image of the retina 127. In particular, a method for acquiring a polarization OCT image (a plane in parallel with the optical axis, i.e., the XZ plane) by forming a tomographic image using polarization parameters (one of optical characteristics of the fundus tissue) will be described below.

Figure 2A:
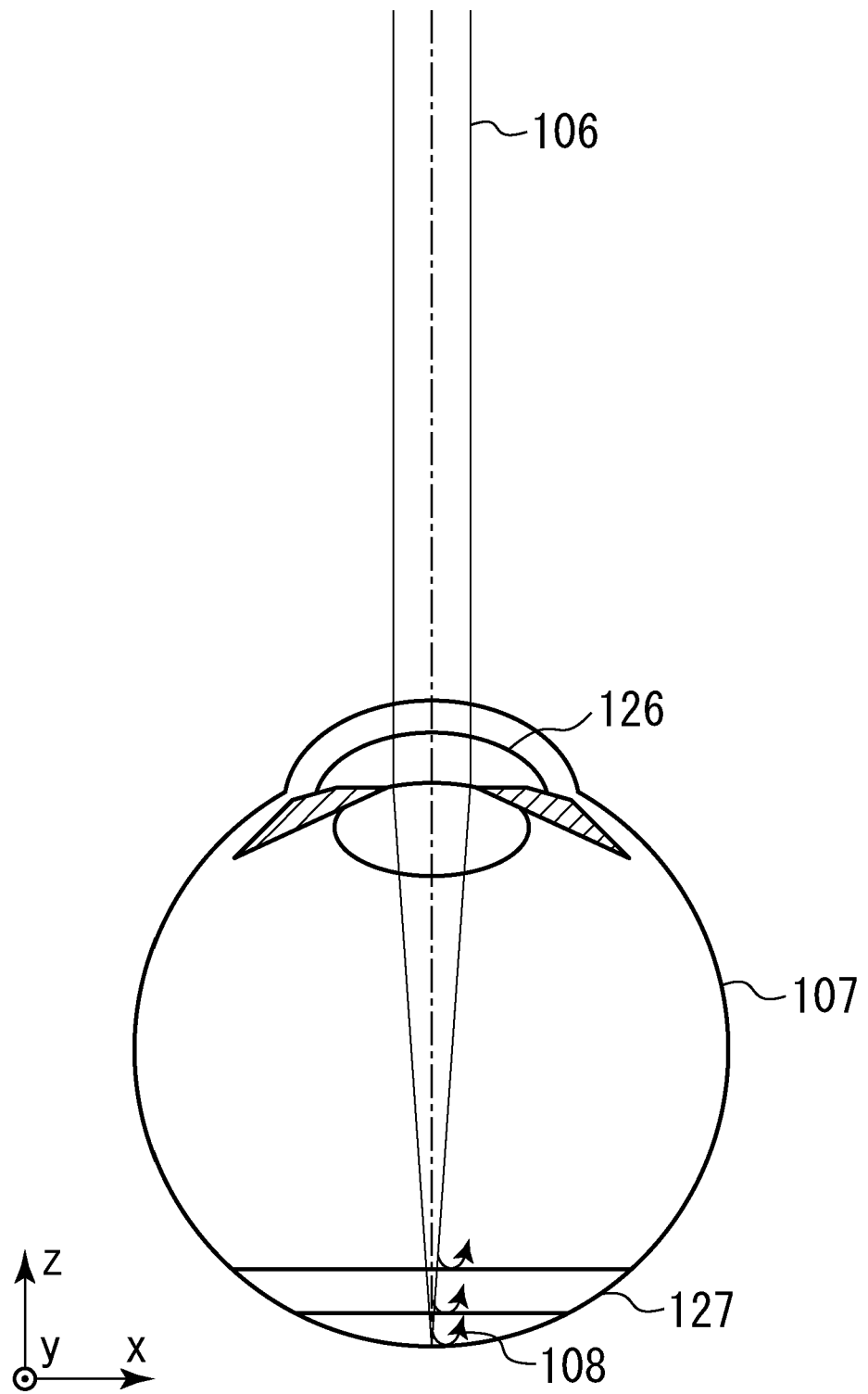
FIG. 2A illustrates a method for acquiring a tomographic image by the OCT apparatus according to the first exemplary embodiment of the present invention.

FIG. 2A is a schematic view illustrating the subject's eye 107 being observed by the OCT apparatus 100. As illustrated in FIG. 2A, the measuring beam 106 passes through the cornea 126 and then enters the retina 127. Then, the return beam 108 is produced by reflection and scattering at various positions and reaches the line camera 139 with time delays at respective positions.

When optical pathlength of the reference beam is close to optical pathlength of the measuring beam to some extent, an interference fringe that can be sampled for the pixel pitch is detected corresponding to the wavelength width of the light source 101, by the line camera 139. As mentioned above, the line camera 139 acquires a spectrum area interference fringe on the wavelength axis in parallel for each polarized beam.

Then, the interference fringe (information on the wavelength axis) is converted into an interference fringe on the optical frequency axis in consideration of the characteristics of the line camera 139 and the light transmission type grating 141. Further, information about the depth direction is acquired by applying the inverse Fourier transform to the converted interference fringe on the optical frequency axis.

Figure 2B:
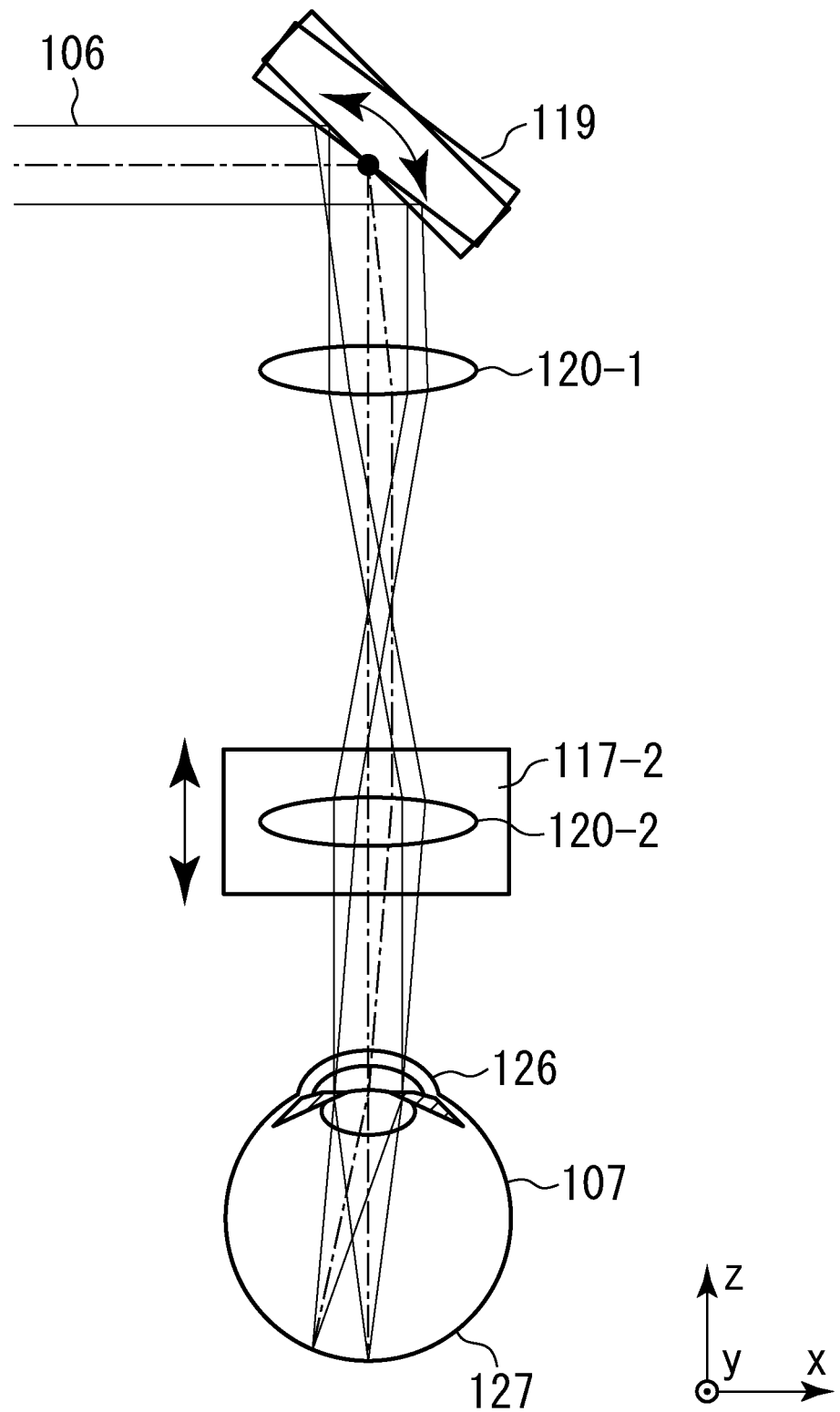
FIG. 2B illustrates a method for acquiring a tomographic image by the OCT apparatus according to the first exemplary embodiment of the present invention.

As illustrated in FIG. 2B, by detecting an interference fringe while driving the XY scanner 119, an interference fringe can be obtained at respective X-axis positions, i.e., information about the depth direction at respective X-axis positions is obtained.

When interference signals of the split beams 175-1 and 175-2 have amplitudes $A_H$ and $A_V$, respectively, a reflectance R of an intensity OCT image (ordinary OCT image) can be represented by formula (1). Non Patent Literature 1 is quoted in this case.

$$R \text{ is proportional to } A_H^2 + A_V^2 \quad (1)$$

Retardation delta and orientation theta which are polarization parameters forming the polarization OCT image can be represented by formulas (2) and (3), respectively.

$$\text{Delta} = \arctan[A_V/A_H] \quad (2)$$

$$\text{Theta} = (180 - \text{delta phi})/2 \quad (3)$$

where phi is a phase of the split beams 175-1 and 175-2, and delta phi is a phase difference between the amplitudes $A_H$ and $A_V$ (delta phi=phiH−phiV).

Figure 2C:
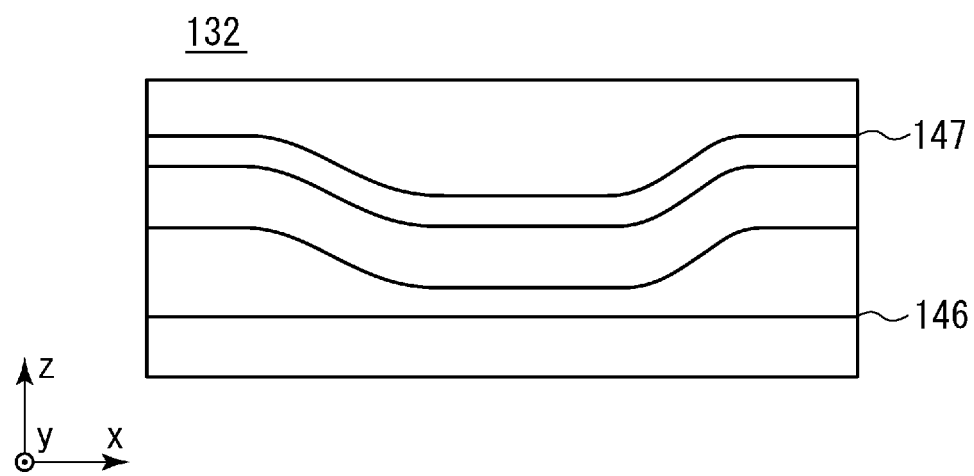
FIG. 2C illustrates a method for acquiring a tomographic image by the OCT apparatus according to the first exemplary embodiment of the present invention.

As a result, formula (1) gives a two-dimensional distribution of the intensity of the return beam 108 in the XZ plane, i.e., a tomographic image 132 (FIG. 2C). As mentioned above, the tomographic image 132 is formed of intensities of the return beam 108 arranged in array form. For example, this intensity is displayed according to the gray scale. FIG. 2C emphasizes only boundaries in the obtained tomographic image 132. The tomographic image 132 includes a pigment epithelium layer 146 and an inner limiting membrane 147.

Formulas (2) and (3) give a two-dimensional distribution of the polarization direction of the return beam 108 on the XZ plane, i.e., a polarization OCT image. In particular, formula (2) gives a retardation image with which a relative phase delay between polarized beams is rendered. Formula (3) gives an orientation image which indicates change in polarization direction. By forming a polarization OCT image in this way, minute changes in the fundus tissue as well as change in the fibrous structure presumed to have large birefringence can be made.

As represented by formulas (2) and (3), retardation delta and orientation theta are calculated from the amplitude and phase of the interference beam, and therefore simultaneously detecting them correctly and stably is essential for forming a polarization OCT image.

By splitting the interference beam (formed by combining the measuring beam 106 with the reference beam 105) into two split beams for each polarized beam and inputting them to the diffraction grating 141 with the polarization directions aligned in this way, it becomes unnecessary to take into consideration the polarization dependence of the diffraction efficiency of the diffraction grating 141 for the two split beams. As a result, the diffraction efficiency of the diffraction grating 141 can be conformed only to a predetermined polarized beam, making it easier to optimize the design of the diffraction grating 141 and accordingly to optimize measurement sensitivity of the OCT apparatus 100. This also makes it easier to achieve the same measurement sensitivity for the two split beams, enabling the acquisition of polarization parameters with higher accuracy. Further, aliasing due to a difference in measurement sensitivity can be prevented.

Polarization directions of the two split beams 175-1 and 175-2 can be easily aligned when the polarization maintaining fibers 134-5 and 134-6 are disposed relative to the diffraction grating 141 such that the polarization directions of the two split beams 175-1 and 175-2 guided by the polarization maintaining fibers 134-5 and 134-6, respectively, coincide with each other.

When the two split beams 175-1 and 175-2 are input to the same position of the diffraction grating 141, the space of the diffraction grating can be effectively utilized.

Further, the two split beams 175-1 and 175-2 are input to one line camera 139 to measure their intensities, so that a polarization OCT apparatus can be configured with a simplified optical setup.

In a second exemplary embodiment, an OCT apparatus 100 to which the present invention is applied will be described below. In the present exemplary embodiment, a so-called polarization OCT apparatus is configured, which has a similar optical setup to the first exemplary embodiment except the measurement system for measuring an interference beam. Therefore, descriptions of the similar optical setup will be omitted and only the measurement system will be described below.

Figure 3:
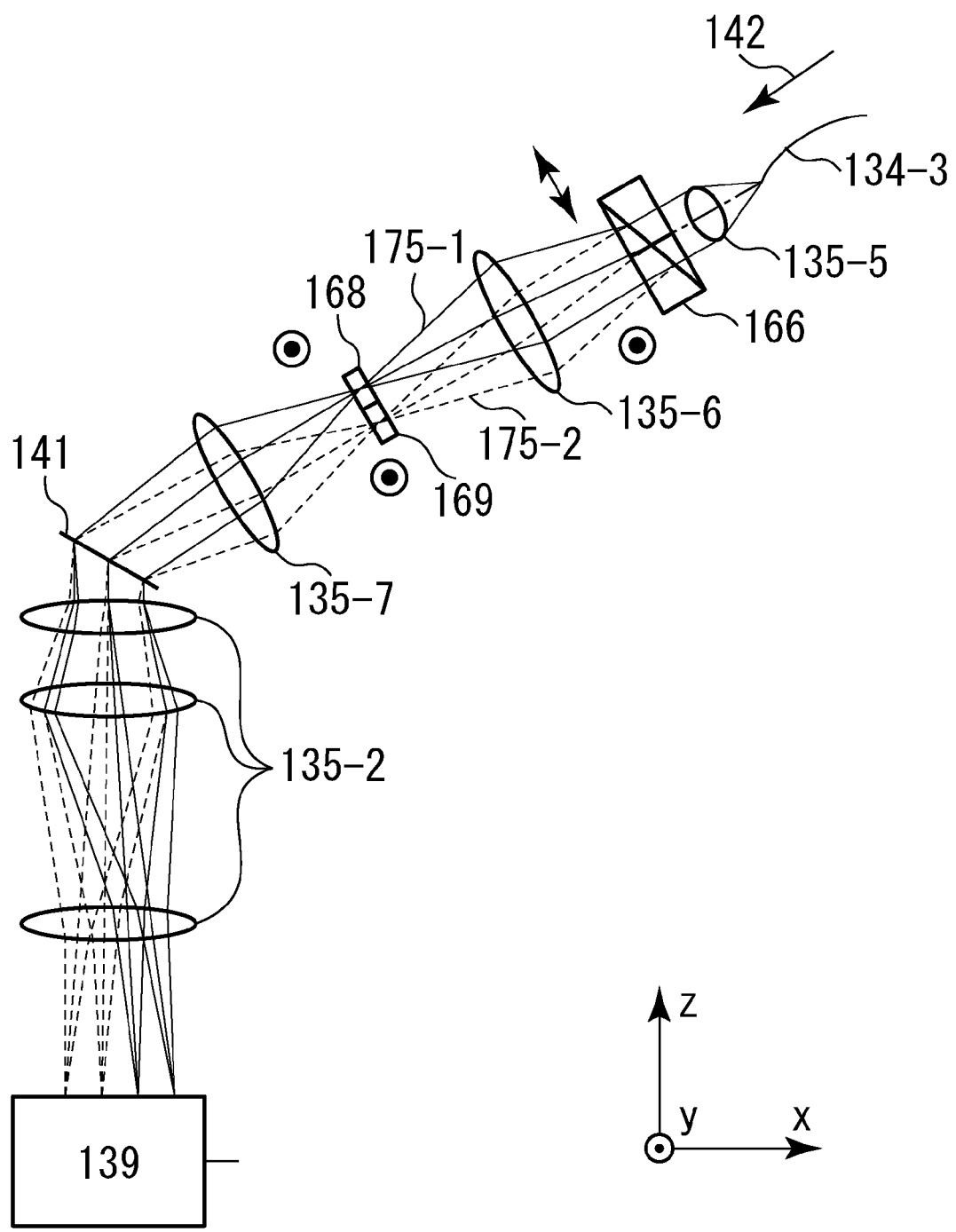
FIG. 3 illustrates a detection system of an OCT apparatus according to a second exemplary embodiment of the present invention.

A configuration of the measurement system in the OCT apparatus 100 according to the present exemplary embodiment will be described below with reference to FIG. 3. The combined beam 142 formed by the optical coupler 131 passes through the polarization maintaining fiber 134-3 and then is led to a lens 135-5. Then, the combined beam 142 reaches a Wollaston prism 166. The combined beam 142 is split into a split beam 175-1 (a linearly-polarized beam in the XZ plane direction (direction in parallel with paper plane)) and a split beam 175-2 (a linearly-polarized beam in the Y-axis direction (direction perpendicular to paper plane)) by the Wollaston prism 166.

The split beam 175-1 passes through a lens 135-6 to be condensed and then is input to a lambda/2 plate 168. The split beam 175-1, when its polarization direction is rotated by 90 degrees by the lambda/2 plate 168, becomes a linearly-polarized beam in the Y-axis direction.

The split beam 175-2 passes through the lens 135-6 to be condensed and then is input to an optical path compensation plate 169. The optical path compensation plate 169 compensates the optical path length or dispersion with respect to the lambda/2 plate 168.

Then, the split beams 175-1 and 175-2 enter a lens 135-7 to become parallel beams and then reach the light transmission type grating 141. The parallel beams are split and diffracted for respective wavelengths by the light transmission type grating 141, condensed by the lenses 135-2, and then reach different positions on the line camera 139. In this case, each of the split beams 175-1 and 175-2 enters the light transmission type grating 141 in the same polarization direction (i.e., as a linearly-polarized beam in the Y-axis direction). Therefore, it becomes unnecessary to take into consideration the polarization dependence of the diffraction efficiency of the light transmission type grating 141, enabling the optimization to polarized beams (linearly-polarized beams in the Y-axis direction) input to the light transmission type grating 141.

The line camera 139 detects the light intensity of each of the split beams 175-1 and 175-2 for respective positions (wavelengths). Specifically, a spectrum area interference fringe on the wavelength axis can be observed by the line camera 139.

The detected light intensity of each of the split beams 175-1 and 175-2 is input to the personal computer 125 via the frame grabber 140. The personal computer 125 performs data processing to form a tomographic image and displays it on a display screen (not illustrated).

The line camera 139 is provided with 2048 pixels to obtain the light intensity for respective wavelengths (1024 divisions) of each of the split beams 175-1 and 175-2.

In the present exemplary embodiment, although each of the split beams 175-1 and 175-2 enters the light transmission type grating 141 as a linearly-polarized beam in the Y-axis direction, the optical setup is not limited thereto as long as the polarization directions of the split beams 175-1 and 175-2 coincide with each other, whatever the polarization direction.

As mentioned above, the polarization directions of the two split beams 175-1 and 175-2 can be accurately aligned by splitting an interference beam into two split beams using a Wollaston prism and providing a lambda/2 plate in an optical path of one split beam and a compensation plate in an optical path of the other split beam. Although a Wollaston prism is used as a polarization beam splitter in the present exemplary embodiment, the polarization beam splitter is not limited thereto, but may be any type of polarization beam splitter as long as it splits an interference beam for each polarized beam, for example, a Savart plate or a Glan-Thompson prism may be utilized.

The present invention is achieved also by performing the following processing. Specifically, software (programs) for implementing the functions of the above-mentioned exemplary embodiments is supplied to a system or apparatus via a network or various memory media, and a computer (or central processing unit (CPU), micro processing unit (MPU), etc.) of the system or apparatus reads and executes the programs.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2010-156919 filed Jul. 9, 2010, which is hereby incorporated by reference herein in its entirety.

The invention claimed is:

1. An optical tomographic imaging apparatus comprising:
   a polarization beam splitter that splits a combined beam into first and second beams having different polarization directions, the combined beam being formed by combining a return beam from an object with a reference beam corresponding to the measuring beam, the object being irradiated with the measuring beam;
   a polarization adjuster that adjusts at least one of the polarization directions of the first and second beams so that the polarization directions of the first and second beams are aligned with each other;
   a common diffraction grating configured to separately disperse the first and second beams in the adjusted polarization direction;
   a detector that separately detects the first and second dispersed beams; and
   a processor that acquires a tomographic image indicating polarization information of the object based on the first and second detected beams.

2. The optical tomographic imaging apparatus according to claim 1, wherein the polarization adjuster comprises:
   a first polarization maintaining fiber configured to guide the first beam; and a second polarization maintaining fiber configured to guide the second beam, wherein a relative angle formed between light-emitting ends of the first and second polarization maintaining fibers is adjusted to irradiate the diffraction grating with the first and second beams in an aligned polarization direction.

3. The optical tomographic imaging apparatus according to claim 1, wherein the polarization adjuster comprises:

a polarization rotator disposed in an optical path of the first beam that rotates the polarization direction of the first beam to coincide it with the polarization direction of the second beam; and a dispersion compensator disposed in an optical path of the second beam that compensates the dispersion of the first beam produced by the polarization rotator.

4. The optical tomographic imaging apparatus according to claim 1, wherein the irradiation beam corresponding to the first beam is irradiated at an irradiation position on the diffraction grating of the irradiation beam corresponding to the second beam.

5. The optical tomographic imaging apparatus according to claim 1, wherein the detector detects, in different areas of a common sensor, beams from the diffraction grating corresponding to the first and second beams respectively.

6. The optical tomographic imaging apparatus according to claim 1, further comprising:

a first polarization changing device disposed in an optical path of the reference beam to change the polarization direction of the reference beam; and a second polarization changing device disposed in an optical path of the measuring beam to change the polarization direction of the measuring beam.

7. The optical tomographic imaging apparatus according to claim 6, wherein the first polarization changing device changes the reference beam into a linearly-polarized beam, and wherein the second polarization changing device changes the measuring beam into a circularly-polarized beam.

8. The optical tomographic imaging apparatus according to claim 4, wherein the polarization adjuster irradiates a same irradiation position on the diffraction grating at different incident angles with beams corresponding to the first and second beams respectively.

9. An optical tomographic imaging method comprising:

splitting a combined beam into first and second beams having different polarization directions, the combined beam being formed by combining a return beam from an object with a reference beam corresponding to the measuring beam, the object being irradiated with the measuring beam;

adjusting at least one of the polarization directions of the first and second beams so that the polarization directions of the first and second beams are aligned with each other;

separately dispersing the first and second beams in the adjusted polarization direction;

separately detecting the first and second dispersed beams; and acquiring a tomographic image indicating polarization information of the object based on the first and second detected beams.

* * * * *